United States Patent [19]

Grignard

[11] 3,954,846
[45] May 4, 1976

[54] NEW QUATERNARY AMMONIUM SALTS OF MALIC ACID AND THEIR APPLICATION IN COSMETICS

[75] Inventor: Robert Grignard, Cap D'Ail, France

[73] Assignee: Agence Nationale de Valorization de la Recherche (ANVAR), Neuilly-sur-Seine, France

[22] Filed: Dec. 23, 1974

[21] Appl. No.: 535,713

[30] Foreign Application Priority Data
Dec. 21, 1973  France .............................. 73.45986

[52] U.S. Cl. ......................... 260/501.15; 424/316; 424/329; 252/117
[51] Int. Cl.$^2$ .................. C07C 87/30; C07C 87/62; C07C 87/68
[58] Field of Search ............................... 260/501.15

[56] References Cited
UNITED STATES PATENTS 3,578,667  5/1971  Wakeman et al. ............. 260/501.15
3,879,350  4/1975  Suzuki et al. .................. 260/501.15

Primary Examiner—Joseph E. Evans
Assistant Examiner—Nicky Chan
Attorney, Agent, or Firm—McDougall, Hersh & Scott

[57] ABSTRACT

Quaternary ammonium salts of malic acid having the formula:

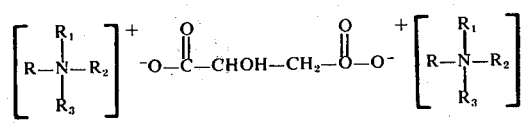

where: R is a monovalent aliphatic hydrocarbon radical, saturated or unsaturated, of from 8 to 20 carbon atoms but preferably of 12 to 18 carbon atoms; $R_1$, $R_2$, $R_3$ may be identical or different and each represents a lower alkyl radical or an aryl radical. The salts find use in cosmetics as a source of the malic ions necessary to the energy process in cellular metabolism. These salts insure a better intracellular penetration of malic ion and improve the stability of creams and other cosmetic emulsions.

5 Claims, No Drawings

NEW QUATERNARY AMMONIUM SALTS OF MALIC ACID AND THEIR APPLICATION IN COSMETICS

The subject of this invention is new quaternary ammonium salts of malic acid having the formula:

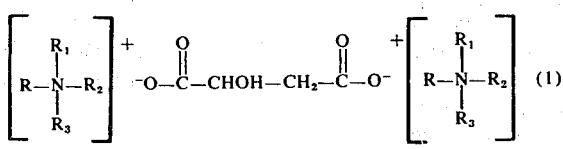

where: R is a monovalent aliphatic hydrocarbon radical, saturated or unsaturated, of 8 to 20 carbon atoms, preferably of 12 to 18 carbon atoms; $R_1$, $R_2$, $R_3$ may be identical or different and each represents a lower alkyl radical of at most 4 carbon atoms, or an aryl radical. In particular, R is the lauryl, myristyl, cetyl or aleyl radical, and $R_1$, $R_2$, $R_3$ each designate a methyl, ethyl, propyl, isopropyl, phenyl or benzyl radical.

The quaternary ammonium salts of malic acid may be prepared by reaction of maleic acid with the corresponding hydroxide of the quaternary ammonium salt:

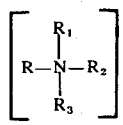

in aqueous medium in the presence of ethanol or isopropanol.

The corresponding hydroxide of the quaternary ammonium salt may be prepared in situ by reaction of the corresponding halide of the quaternary ammonium salt with an excess of silver hydroxide, preferably freshly prepared.

The new quaternary ammonium salts of malic acid of this invention are especially useful in cosmetics. It is known that malic acid is one of the fundamental factors in cellular metabolism, and as such it presents considerable interest in cosmetics, especially in the manufacture of cleansing creams.

However, malic acid cannot be used in the free state or neutral state without certain precautions, because it interferes as an electrolyte and, in reducing the stability of the emulsions, it can lead to break-up of the emulsion. In fact, as the electric conductivity of the aqueous phase of the emulsion increases, the electrostatic charges on the particles of the oily phase in suspension are reduced. This causes a lowering of the forces of repulsion which may thus become less than the Van der Waals forces of attraction, and this inevitably leads to the break-up of the emulsion.

Furthermore, the intracellular penetration of malic acid, which is soluble in water and insoluble in oils, is relatively weak.

In order to overcome these disadvantages, it has been suggested that fat-soluble esters of malic acid be used in place of the said acid to achieve a better intracellular penetration of malic ion. Nevertheless, these esters have a tendency to hydrolyze in aqueous solution, which affects the stability of cosmetic emulsions. Moreover, they are not surface-active, and are neither bactericidal nor anti-fungicidal.

The quaternary ammonium salts of malic acid of this invention are particularly valuable for the care of the skin in general, and especially in cosmetics, for the following reasons:

They supply the malic ion necessary to the energy process in cellular metabolism.

This malic ion penetrates the skin rapidly through the sebum, thanks to the lipophilic quaternary ammonium ion to which it is in polarly bonded.

These substances, by virtue of their hydrophilic anion and their lipophilic cation, are remarkably surface-active; they therefore have:

great ease of application to the surface of the skin and hence a better intracellular penetration.

greater stability of the creams in which they are incorporated, by lowering of the surface-tension at the oil-water interface and reduction of the volume of droplets in emulsion.

These substances, being quaternary ammonium compounds, are strongly bactericidal and fungicidal. They therefore are efficient self-preservatives.

Further, these substances, being water-soluble, may be used in aqueous solution, for example in hair lotions.

The application will be illustrated by the following examples, which are given by way of illustration and not by way of limitation.

EXAMPLE 1

CETYLTRIMETHYLAMMONIUM MALATE

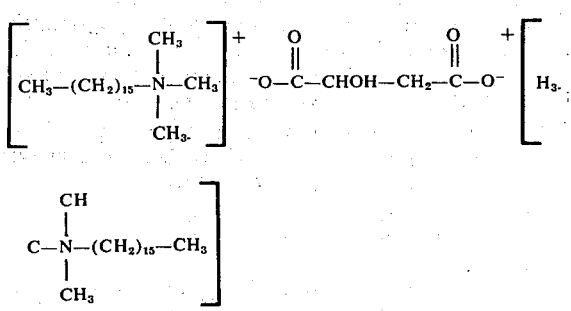

Silver nitrate (600 g) is dissolved in purified water (2.5 liters). Caustic soda ($d = 1.33$, 400 g) is added, and the solution is agitated for 30 minutes in the absence of light. It is filtered, the precipitate of silver hydroxide is washed with water and is placed in an aqueous solution of cetyltrimethylammonium chloride (25%, 3.65 kg).

The solution is stirred for 16 hours, in the absence of light, after which absolute ethanol (20 liters) is added. It is stirred for 2 minutes, then filtered to eliminate the silver chloride formed and the excess of silver hydroxide, and this residue is washed with absolute ethanol (300 ml).

To the mother liquors, active carbon (50 g) is added. The mixture is stirred for 15 minutes, filtered and the residue washed with absolute ethanol (200 ml).

To the cetyltrimethylammonium hydroxide obtained, maleic acid (191 g) is added and the mixture is stirred until completely dissolved.

The pH of an aqueous solution to 1/5 strength should be near 6.

The mixture is concentrated to about 3 liters by distillation of ethanol, then evaporated to dryness under vacuum (60°C, 15 mm Hg).

The cetyltrimethylammonium malate is obtained as a white mass of waxy consistency, soluble in water and alcohols, insoluble in petroleum ether, benzene and cyclohexane.

Empirical formula: $C_{42}H_{88}O_3N_2$

Molecular weight: 701.25

Composition: cetylmethylammonium ion: 81.17%
malic ion: 18.83%

In this example, freshly prepared silver hydroxide was used to increase the reactivity.

Absolute ethanol was added to break up the foam which would make concentration impossible; ethanol may be replaced by smaller quantities (about 1 liter) of isopropanol.

Finally, the use of silver hydroxide may be avoided by using anion exchangers of the polystyrene/quaternary ammonium type (for example, Amberlite I R A 400) to fix the chlorine.

Under these conditions, the volumes are greater, and the consumption of alcohol correspondingly higher.

For use in cosmetics, cetyltrimethylammonium malate is applied in aqueous solution (25% w/w).

This solution is limpid, colorless to light yellow, almost odorless, has a very bitter taste and froths copiously on agitation.

The pH of the solution is near 6.

Reactions for identification -

1. On addition of calcium nitrate, a viscous gel is formed. To a test-tube containing the malate solution (25%, 1 ml) is added water (5 ml), an aqueous solution of calcium nitrate (30%, 1 ml) and the solution is stirred. A viscous gel is formed.

2. The test mixture above is boiled vigorously. A rancid odor, characteristic of fatty alcohols, develops.

The sumagent alcohol is separated: M.P. 49°C.

3. In the presence of reagents containing potassium iodobismuthite, an orange coloration and precipitate are obtained: To a test-tube containing the malate solution (25%, 1 ml), water (5 ml) is added and then a few drops of the potassium iodobismuthite reagent (R).

In a graduated flask (1000 ml) is placed successively:
finely powdered bismuth (20.8 g)
iodine (38.1 g)
potassium iodide (200 g)
water (600 ml)

The mixture is stirred until all is dissolved (about 30 minutes), and the volume made up to 1000 ml with water.

An orange precipitate and coloration appear.

4. In the presence of VS blue (CI 42045), blue solutions are obtained, the color of which may be extracted by organic solvents. To a test-tube containing cetyltriethylammonium malate solution (25%, 5 ml) diluted to 1/1000 strength with water is added:

an aqueous solution of VS blue (0.2 mg/ml, 5 ml) (VS blue (CI 42045) is the sodium salt of [[α-[p-(dimethylamino)phenyl]-disulphobenzylidene-2,4]-4cyclohexadiene-2.5-ylidine-1]diethylammonium)

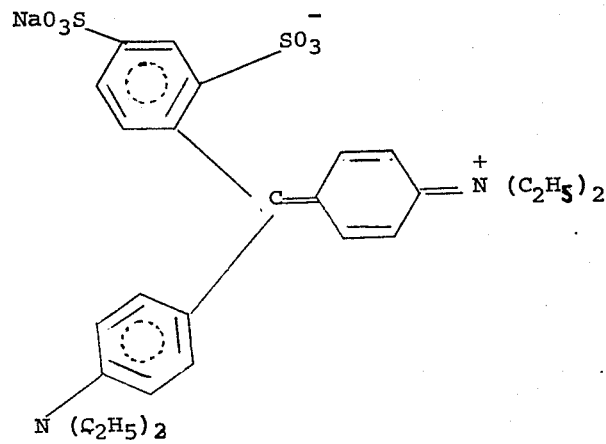

hydrochloric acid (R) (0.05 N, 1 ml)
a mixture (10 ml) of composition by volume
benzene 65
secondary butanol 35

The whole is stirred and allowed to stand.

The upper solvent phase is colored turquoise blue, whereas there is almost no coloration in a control solution containing no cetyltrimethylammonium malate.

5. Addition of ferric chloride gives a yellow color. To a test-tube containing the malate solution (25%, 1 ml) water (5 ml) is added and then 2 drops of an aqueous solution of ferric chloride (26%) (R).

A yellow color appears.

6. Addition of sulphonaphthyl reagent gives a green-yellow color, then yellow changing to orange on aqueous dilution. To a test-tube containing the malate solution (25%, 1 ml) the sulphonaphthyl reagent (2 ml) is added (β naphtol (1 g) in concentrated sulphuric acid (R) (100 g) and the mixture is heated gently.

A green-yellow color appears, then yellow changing to orange on dilution with water.

These cetyltrimethylammonium malate solutions may be titrated by potentiometry in an anhydrous acetic medium as follows:

In a beaker (100 ml), is placed malate solution (approx. 1 g) weighed to an accuracy of 0.1 mg. Anhydrous acetic acid (R) (80 ml) is added, and the solution is concentrated at atmospheric pressure down to about 40 ml to remove water by azeotropy.

This is titrated by potentiometry with perchloric acid (0.1 N) in an anhydrous acetic medium $$\text{Strength \%} = \frac{M \times N \times V}{P \times n} \times 100$$

where
N: normality of perchloric acid: (0.1)
V: volume (ml) of perchloric acid consumed
M: molecular weight of cetyltrimethylammonium malate: 701.25
P: mass of specimen (mg)
n: valency of cetyltrimethylammonium malate (2)

$$\text{Strength \%} = \frac{V}{P} \times 3,506.25$$

EXAMPLE 2

LAURYLTRIMETHYLAMMONIUM MALATE

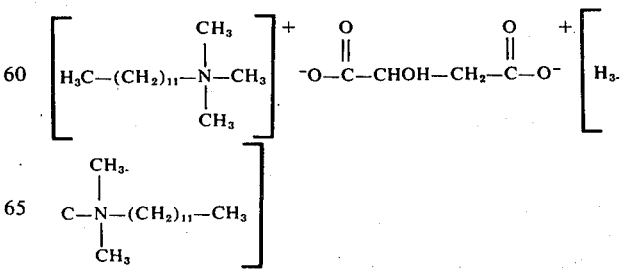

The procedure followed is that of Example 1, but using maleic acid (227.6 g) and an aqueous solution of lauryltrimethylammonium chloride (25%, 3.576 g).

Lauryltrimethylammonium malate is obtained as a white mass of waxy consistency, fragrant, soft, soluble in water, methanol and ethanol.

Empirical formula: $C_{34}H_{72}O_5N_2$
Molecular weight: 589.25
Composition: lauryltrimethylammonium ion 77.60%
malate ion 22.40%

Lauryltrimethylammonium malate is supplied in aqueous solution (25% w/w).

This solution is limpid, colorless to light yellow, almost odorless, has a very bitter taste and froths copiously on agitation. The pH of the solution is near 6.

The reactions for identification are the same as for the substance in Example 1, with the exception of reaction 2 where the suragent alcohol separated has a melting point of 24°C.

EXAMPLE 3
CETYLDIMETHYLBENZYLAMMONIUM MALATE

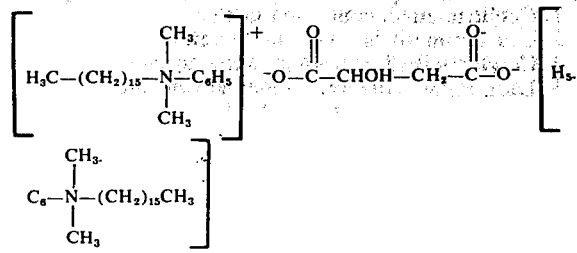

The procedure followed is that of Example 1, but using maleic acid (162.5 g) and an aqueous solution of cetyldimethylbenzylammonium chloride (25%, 3.696 g).

Cetyldimethylbenzulammonium malate is obtained as a white powder of waxy consistency, soluble in water and alcohols.

Empirical formula: $C_{52}H_{92}O_5N_2$
Molecular weight: 825.25
Composition: cetyldimethylbenzylammonium ion 84.0%
malic ion 16.0%

Cetyldimethylbenzylammonium malate is supplied in aqueous solution (25% w/w). This solution is limpid, colorless to light yellow, almost odorless, has a very bitter taste and froths copiously on agitation. The pH of the solution is near 6.

The reactions for identification are the same as for the substance in Example 1, and the following further reaction may be added:

Into an aqueous solution of cetyldimethylammonium malate, is placed a methylene blue iodomercurate reagent paper. A displacement of the iodomercurate ion is observed and the blue coloration passes into the solution.

EXAMPLE 4
LAURYLDIMETHYLBENZYLAMMONIUM MALATE

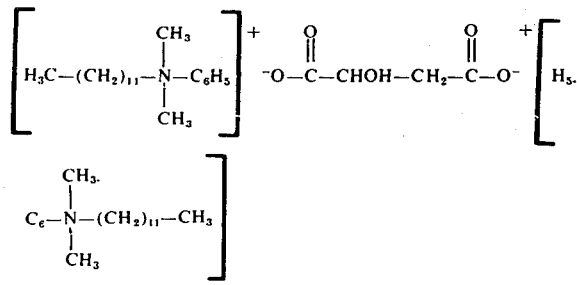

The procedure followed is that of Example 1, but using maleic acid (188 g) and an aqueous solution of lauryldimethylbenzylammonium chloride (25%, 3.646 g).

Lauryldimethylbenzylammonium malate is obtained as a white mass of waxy consistency, soluble in water and alcohols.

Empirical formula: $C_{44}H_{76}O_5N_2$
Molecular weight: 713.25
Composition: lauryldimethylbenzylammonium ion 18.52%
malic ion 81.48%

The lauryldimethylbenzyl ammonium chloride is supplied in aqueous solution (25% w/w). This solution is limpid, colorless to light yellow, almost odorless, has a very bitter taste and froths copiously on agitation. The pH of the solution is near 6.

The reactions for identification are the same as for the substance in Example 2, and the following further reaction may be added:

Into an aqueous solution of lauryldimethylbenzylammonium malate is placed a methylene blue iodomercurate reagent paper. A displacement of the iodomercurate anion is observed and the blue coloration passes into the solution.

The use in cosmetics of the quaternary ammonium salts of malic acid of this invention is illustrated below. In the composition of cosmetics given under these non-exhaustive examples, the average content in quaternary ammonium salts of malic acid is approximately 0.5 to 3% by weight.

| Formula for cleansing cream | Parts by weight |
|---|---|
| Cetyltrimethylammonium malate (aqueous solution, 25%) | 40 |
| Phytohormones | 2 |
| Natural or synthetic fats: | |
| Avocado oil | 80 |
| Mono and diglycerides of palmitic acid | 60 |
| Mono and diglycerides of stearic acid | 60 |
| Isopropyl myristate | 20 |
| Octyl - 2 dodecanol | 130 |
| Glycerol monostearate | 5 |
| Non-ionic surface-active substances: | |
| Ketyl alcohol polyglycolether | 5 |
| Stearyl alcohol polyglycolether | 5 |
| Olyl alcohol polyglycolether | 10 |
| Stabilizer: undecylenic diethanolamide | 2 |
| Perfume | 3 |
| Redistilled water | 578 |
| | 1,000 |

| Formula for hair lotion | Parts by weight |
|---|---|
| Cetyltrimethylammonium malate (aqueous solution, 25%) | 80 |
| Panthenol | 2 |
| Perfume | as required |
| Colorant | as required |
| Distilled water as required up to | 1 liter |

| Formula for hair lotion | Parts by weight |
|---|---|
| Lauryltrimethylammonium malate (aqueous solution, 25%) | 80 |
| Pathenol | 2 |
| Perfume | as required |
| Colorant | as required |
| Distilled water as required up to | 1 liter |

| Formula for hydrating cream | Parts by weight |

| Formula for cleansing cream | Parts by weight |
|---|---|
| Cetyltrimethylbenzylammmonium malate (aqueous solution 25%) | 20 |
| Hydrated proteins | 10 |
| Natural or synthetic fats: | |
| Ivorine | 20 |
| Oil of sweet almonds | 60 |
| Stearic acid diglyceride | 120 |
| Isopropyl myristate | 20 |
| n-decyl alcohol | 130 |
| Non-ionic surface-active substances: | |
| Oleic alcohol polyglycolether | 10 |
| Ketyl alcohol polyglycolether | 10 |
| Stearyl alcohol polyglycolether | 10 |
| Stabilizer - undecyl diethanolamide | 2 |
| Purified water | 586 |
| Perfume | 2 |
| | 1,000 |

| Formula for shampoo treatment | Parts by weight |
|---|---|
| Lauryldimethylbenzylammonium malate (aqueous solution 25%) | 20 |
| Triethanolamine laurylsulphate (40% solution) | 500 |
| Lauric acid diethanolamide | 200 |
| Perfume | 2 |
| Purified water and colorant | 278 |
| | 1,000 |

I claim:
1. Quaternary ammonium salt of malic acid having the following formula:

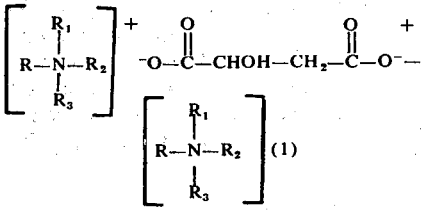

where: R is a radical selected from the group consisting of lauryl, myristyl, cetyl and oleyl, and $R_1$, $R_2$ and $R_3$ each is a radical selected from the group consisting of methyl, ethyl, propyl, isopropyl, phenyl and benzyl.

2. Cetyltrimethylammonium malate.
3. Lauryltrimethylammonium malate.
4. Cetyldimethylbenzylammonium malate.
5. Lauryldimethylbenzylammonium malate.

* * * * *